United States Patent [19]

Shafiee et al.

[11] Patent Number: 5,612,217
[45] Date of Patent: Mar. 18, 1997

[54] STREPTOMYCES SP. MA 7074 (ATCC 55605) USED FOR MICROBIAL SYNTHESIS OF HIV PROTEASE INHIBITORS

[75] Inventors: Ali Shafiee, Westfield; Shieh-Shung T. Chen, Morganville; Byron H. Arison, Watchung; Randall R. Miller, Somerset; George M. Garrity, Westfield; Brian Heimbuch, North Brunswick, all of N.J.

[73] Assignee: Merck & Co., Inc., Rahway, N.J.

[21] Appl. No.: 328,221

[22] Filed: Oct. 25, 1994

[51] Int. Cl.[6] ........................................ C12N 1/20
[52] U.S. Cl. ...................... 435/253.5; 435/118; 435/886
[58] Field of Search ........................... 435/253.5, 886

[56] References Cited

U.S. PATENT DOCUMENTS

| | | | |
|---|---|---|---|
| 5,116,756 | 5/1992 | Dumont et al. | 435/253.5 |
| 5,194,378 | 3/1993 | Salituro et al. | 435/118 |
| 5,221,625 | 6/1993 | Chen et al. | 435/253.5 |
| 5,272,068 | 12/1993 | Ruby et al. | 435/118 |
| 5,413,999 | 5/1995 | Yacca et al. | 514/231.5 |

FOREIGN PATENT DOCUMENTS

05541168A1 2/1992 European Pat. Off. .

*Primary Examiner*—Herbert J. Lilling
*Attorney, Agent, or Firm*—Mel Winokur; Mary A. Appollina

[57] ABSTRACT

Biotransformation products of a fermentation with culture MA7074 are potent HIV protease inhibitors. These products are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

1 Claim, No Drawings

STREPTOMYCES SP. MA 7074 (ATCC 55605) USED FOR MICROBIAL SYNTHESIS OF HIV PROTEASE INHIBITORS

BACKGROUND OF THE INVENTION

The present application is related to Merck 19275, 18996 and 18996IA.

The present invention is concerned with a novel process for synthesizing compounds that inhibit the protease encoded by human immunodeficiency virus (HIV), and in particular certain oligopeptide analogs, such as derivatives of Compound J in the Examples below. These compounds are of value in the prevention of infection by HIV, the treatment of infection by HIV and the treatment of the resulting acquired immune deficiency syndrome (AIDS). These compounds are also useful for inhibiting renin and other proteases.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et at., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et at., *Science*, 231, 1567 (1986); Pearl, L. H. et al., *Nature*, 329, 351 (1987)]. Compounds, including certain oligopeptide analogs that can be made from the novel processes of this invention are inhibitors of HIV protease, and are disclosed in EPO 541,168, which published on May 12, 1993. See, for example, Compound J therein.

Previously, the synthesis of Compound J and related compounds was accomplished via a 12-step procedure. This procedure is described in EPO 541,168. The extreme length of this route (12 steps), renders this process time consuming and labor intensive, and it requires the use of many presently expensive reagents and a presently expensive starting material. A route requiring fewer reaction steps and reagents would provide desirable economical and time-saving benefits.

Applicants have identified and synthesized a variety of derivatives of Compound J, by incubating Compound J with a selected microbial system, MA7074. The new compounds are active and potent inhibitors of HIV protease.

The 2,3-cis-hydroxy analogue of Compound J has previously been synthesized by chemical synthesis. Chemical reactions are usually complex, expensive, and due to the usage of various chemicals and solvents are environmentally damaging. The 3-Keto analogue of Compound J is a novel structure and showed less HIV-protease activity than Compound J. Because of the availability of a keto group this compound is useful as starting material for the synthesis of other derivatives.

SUMMARY OF THE INVENTION

Biotransformation products of a fermentation with culture MA7074 are potent HIV protease inhibitors. These products are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

DETAILED DESCRIPTION OF THE INVENTION

A method is disclosed for synthesizing biotransformation products of the Compound J having the structure:

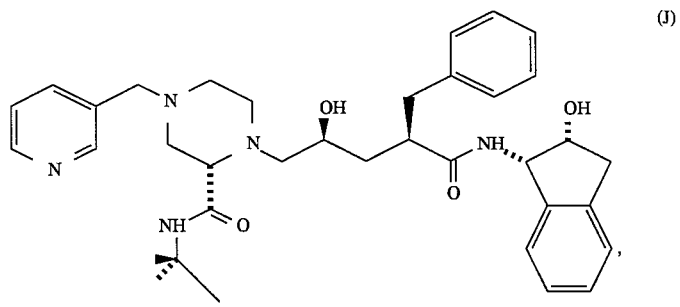

(J)

or salt or hydrate thereof, comprising the steps of
(a) providing a culture of MA7074;
(b) incubating said culture with Compound J;
(c) isolating biotransformation products comprising:

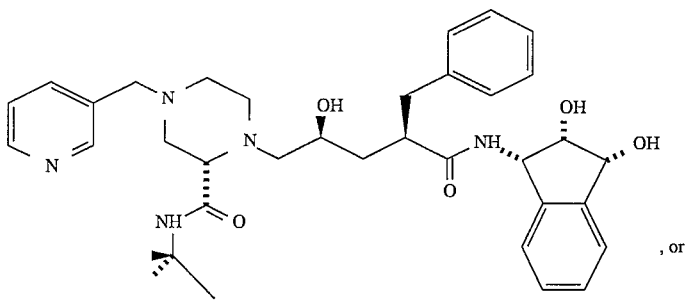

Compound B1

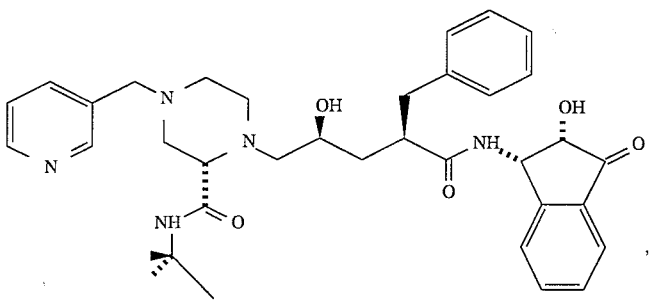

, or

Compound F or salt thereof or hydrate thereof. A preferred compound is Compound F. The purified biotransfomation products of this method are also encompassed by this invention, as well as the chemical compounds.

ATCC Deposit

Before the U.S. filing date of the present application, a sample of the microorganism (Merck Culture Collection MA7074) was deposited at the American Type Culture Collection (ATCC), 12301 Parklawn Drive, Rockville, Md. 20852. The culture access designation is 55605. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

General Characteristics of ATCC

The physical characteristics and taxonomy, including morphological, cultural, biological and physiological characteristics are briefly described hereinbelow.

On the basis of the taxonomic analysis performed thus far, the culture has been assigned to the order Streptomyces.

The following is a general description of *Streptomyces sp.* MA7074 (AS2285, CRA-10-75, ATCC 55605). This culture produces analogs of L-735,524, an inhibitor of HIV protease, by biotransformation. Observations of growth, general cultural characteristics and carbon source utilization were made in accordance with the methods of Shirling and Gottleib (*Internal. J. System. Bacteriol.*, 16, 313–340). Chemical composition of the cells was determined using the methods of Lechevalier and Lechevalier (in *Actinomycete Taxonomy*, A. Dietz and D. W. Thayer, Ed. *Society for Industrial Microbiology*, 1980). Whole cell fatty acids were derivatized and analyzed as methyl esters (FAMEs) by gas chromatography by the procedure of Miller and Berger using a MIDI Microbial Identification System (*Microbial Identification Systems*, Newark Del.). Coloration of the culture was determined by comparison with color standards contained in the Inter-Society Color Council-National Bureau of Standards Centroid Color Charts (US Dept. of Commerce National Bureau of Standards supplement to *NBS Circular*, 553, 1985).

Source

Culture MA7074 was isolated from a soil sample collected beneath a mixed stand of palm trees along the road to Playa Naranja, Santa Rosa Park, Guanacaste PR, Costa Rica.

Chemotaxonomic Characteristics

The peptidoglycan of MA7074 contains LL-diaminopimelic acid. Major whole cell fatty acids are listed in Table 1.

TABLE 1

| Major Whole Cell Fatty Acids Found in MA7074 | |
|---|---|
| Fatty acid | % age |
| 14:0 iso | 7.65 |
| 15:0 iso | 13.31 |
| 15:0 anteiso | 20.86 |
| 15:0 | 3.11 |
| 16:0 iso H | 7.22 |
| 16:0 iso | 24.68 |
| 16:1 cis 9 | 1.73 |
| 16:0 | 2.66 |
| 16:0 9 $CH_3$ | 2.92 |
| 17:0 anteiso C | 3.48 |
| 17:0 iso | 2.41 |
| 17:0 anteiso | 6.55 |

General Growth Characteristics

Good to excellent growth was observed on yeast-extract malt-extract agar, glycerol-asparagine, inorganic salts-starch agar, Sabouraud Maltose agar, oatmeal agar and trypticase soy broth agar. Fair to poor growth was observed on Czapek's agar and tap water agar. Growth occurred at 27° and 37° C. See Table 2.

TABLE 2

Cultural characteristics of Actinomycete sp. MA7074

| Medium | Amount of growth | Aerial mycelium | Soluble pigments | Substrate mycelium |
|---|---|---|---|---|
| Yeast Extract Malt Extract | Good | Light gray (264 l. gray) Spores borne on straight to flexous sporophores | None | Dark orange yellow (72 d. OY) |
| Glucose Aspargine | Good | Medium gray (265 med. Gy) Spores borne on branching, flexous sporophores with occasional knot like structures present | None | Medium yellow (87 m. Y) |
| Inorganic Salts-Starch | Good | Light gray (264 l. gray)Spores borne on branching, flexous sporophores | None | Medium orange yellow (71 m. Y) |
| Oatmeal | Good | White (263 White) Spores borne on branching, flexous sporophores with occasional knot like structures present | None | Light greenish yellow (101 l.g Y) |
| Czapek | Moderate | White (263 White) Spores borne on branching, flexous sporophores with occasional knot like structures present | None | Very yellow (82 v. Y) |
| Tap Water | Fair | White (263 White) Spores borne on branching, flexous sporophores with occasional knot like structures present | None | Pale greenish yellow (84 p. g Y) |
| Peptone Iron | $H_2S$ negative, Melanin negative | | | |

Colony Morphology (On yeast-malt agar at 21d) Substrate mycelium is a dark yellow orange. Aerial spore mass is light gray in color. Colonies are opaque, raised, with an entire edge and matte surface. The colonies are rubbery in texture.

Micromorphology

Aerial mycelia (0.57 μm) arise from substrate mycelia. In mature cultures (7–28d p.i.) the aerial mycelium is long, flexous and branched, terminating in flexous chains of spores. Sporulation occurs on yeast extract malt extract agar, inorganic salts-starch agar, oatmeal, glycerol asparagine agar, Czapek's agar and tap-water agar. The aerial spore mass readily breaks down on all but yeast extract-malt extract agar.

Miscellaneous Physiological Reactions

Culture does not produce $H_2S$ on peptone-iron agar. Melanoid pigments were not formed in either peptone-iron agar or tryptone-yeast extract broth. Starch was not hydrolyzed. Carbon source utilization pattern is as follows: good utilization of L-arabinose, D-fructose, α-D-glucose, inositol, α-D-lactose, β-D-lactose, D-maltose, D-mannitol, D-mannose, D-raffinose, L-rhanmose, sucrose and D-xylose; moderate utilization of D-arabinose. See Table 3.

TABLE 3

Carbon Source Utilization Pattern of Strains MA7074

| Carbon source | Growth |
|---|---|
| D-arabinose | 2 |
| L-arabinose | 3 |
| D-fructose | 3 |
| inositol | 3 |
| α-D-lactose | 3 |
| β-D-lactose | 3 |
| D-maltose | 3 |
| D-mannitol | 3 |
| D-mannose | 3 |
| D-raffinose | 3 |
| L-rhamnose | 3 |
| sucrose | 3 |
| D-xylose | 3 |
| α-D-glucose (control) | 3 |

3 = good utilization,
2 = moderate utilization,
1 = poor utilization,
0 = no utilization Diagnosis Cell wall analysis reveals that MA7074 has a type I cell wall. Morphological studies reveal that the culture produces long chains of spores on flexous sporophores that arise from the aerial mycelium. These are characteristics that are typical for many strains of *Streptomyces sp.* A comparison of the phenotypic data for MA7074 with that of the validly published species of *Streptomyces* in the taxonomic literature shows that this strain bears some resemblance to *Streptomyces albofiavus, Stmy. diastaticus Stmy. rimosus* and *Stmy. rocheii*. However, MA7074 can be readily distinguished from each of these reference strains based upon difference is sporophore morphology (*Stmy. rocheii* and *Stmy. rimosus* have spiral sporophores) and/or carbon source utilization. Comparison of the fatty acid profile of MA7074 against the MIDI actinomycete library (Version 3.7) showed a distant match to *Stmy. cyaneus*.

A cluster analysis was performed with furthest neighbor analysis using Euclidean distance as the metric. The results of this analysis showed MA7074 was distinct from all five of these reference cultures. These findings are consistent with morphological and physiological data. Based upon these findings, MA7074 is a strain of a previously undefined species of *Streptomyces*.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Compounds B1 and F can also be obtained by synthetic organic procedures, by a skilled artisan.

As to the conditions for the production of MA7074 in massive amounts, submerged aerobic cultural conditions are preferred. For the production in small amounts, a shaking or surface culture in a flask or bottle is employed. Furthermore, when the growth is carried out in large tanks, it is preferable to use the vegetative forms of the organism for inoculation in the production tanks in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 10 hours to 64 hours, which may be varied according to fermentation conditions and scales. Preferably, the production cultures are incubated for about 48 hours at 28° C. on a rotary shaker operating at 220 rpm, wherein the pH of the fermentation medium is maintained at 4.85 to harvest.

Preferred culturing/production media for carrying out the fermentation include the following media: Seed medium (KE medium) consisted of: 0.1% dextrose; 1% dextrin; 0.3% beef extract; 0.5% ardamine pH; 0.5% NZ amine type E; 0.005% $MgSO_4 \cdot 7H_2O$, and 0.037% $K_2HPO_4$ with pH adjusted to 7.1 with 0.05% $CaCO_3$. Biotransformation medium (soy-glucose) contained: 2% glucose; 0.5% soya meal; 0.5% yeast extract; 0.5% NaCl; 0.98% MES with pH adjusted to 7.0.

The products can be recovered from the culture medium by conventional means which are commonly used for the recovery of other known substances. The substances produced are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

The compounds of the present invention are useful in the inhibition of HIV protease the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the an of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to four times per day. In one preferred regimen, dosages of 100–400 mg every six hours are administered orally to each patient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV protease inhibitory compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

TABLE C

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc. (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT AIDS, adv, ARC | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| B | Merck (Rahway, NJ) | AIDS, ARC, asymptomatic HIV positive, also in |

TABLE C-continued

| Drug Name | Manufacturer | Indication |
|---|---|---|
| C | Merck (Rahway, NJ) | combination with AZT. AIDS, ARC, asymptomatic HIV positive, also in combination with AZT. |
| Nevirapine | Boehringer Ingelheim | AIDS, ARC, asymptomatic HIV positive, also in combination with AZT. |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246, 738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Somerville, NJ) Immunex (Seattle, WA) | AIDS |
| Granulocyte Macrophage Colony Stimulating Factor | Schering-Plough (Madison, NJ) | AIDS |
| | | AIDS, in combination w/AZT |
| HIV Core Particle Immuno-stimulant | Rorer (Ft. Washington, PA) | seropositive HIV |
| IL-2 Interleukin-2 | Cetus (Emeryville, CA) | AIDS, in combination W/AZT |
| IL-2 Interleukin-2 | Hoffman-La Roche (Nutley, NJ) Immunex | AIDS, ARC, HIV, in combination W/AZT |
| Immune Globulin Intravenous (human) | Cutter Biological (Berkeley, CA) | pediatric AIDS, in combination W/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma W/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination W/AZT |
| rCD4 Recombinant Soluble Human | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination W/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis prevention of |
| Pastille Nystatin Pastille | Squibb Corp. (Princeton, NJ) | oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/ sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Certain compounds of Table C are the following:

Compound B is 6-chloro-4-(S)-cyclopropyl-3,4-dihydro-4-((2- pyridyl)ethynyl)quinazolin-2( 1H)-one;

Compound C is(−)6-chloro-4(S)-trifluoromethyl-1,2-dihydro-4(H)-3,1-benzoxazin-2-one; nevirapine is 11-cyclopropyl-5,11-dihydro-4-methyl6H-dipyrido[3,2-b:2', 3'-e][1,4]diazepin-6-one. Compounds B and C are synthesized by the methods of EP 0,569,083, herein incorporated by reference for this purpose. Nevirapine is synthesized by Klunder, J. M. et al., *J. Med. Chem.*, 35, 1887 (1992); Hargrave, K. D. et at., *J. Med Chem.*, 34, 2231 (1991); Cohen, K. A. et al., *J. Biol. Chem.*, 266, 14670 (1991), all three references herein incorporated by reference.

Preferred combinations are simultaneous or alternating treatments of an inhibitor of HIV protease and a non-nucleoside inhibitor of HIV reverse transcriptase. An optional third component in the combination is a nucleoside inhibitor of HIV reverse transcriptase, such as AZT, ddC or ddI. A preferred inhibitor of HIV protease is Compound F. Preferred non-nucleoside inhibitors of HIV reverse transcriptase include Compound B, Compound C or nevirapine. These combinations may have synergistic effects on limiting the spread of HIV. Preferred combinations include the following (1) Compound F, with a preferred non-nucleoside inhibitor of HIV reverse transcriptase, and, optionally, AZT or ddI or ddC; (2) Compound F, and any of AZT or ddI or ddC.

Assay for Inhibition of Microbial Expressed HIV Protease

Inhibition studies of the reaction of the protease expressed in *Eschericia coli* with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 µl DMSO were added to 25 µl of the peptide solution in water. The reaction is initiated by the addition of 15 µl of 0.33 nM protease (0.11 ng) in a solution of 0.133M Na acetate pH 5.5 and 0.1% bovine serum albumin. The reaction was quenched with 160 µl of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined as $IC_{50}$ from the peak heights of the products. HPLC of the products, independently synthesized, proved quantitation standards and confirmation of the product composition.

CELL SPREAD ASSAY

Inhibition of the spread of HIV in cell culture was measured according to Nunberg, J. H. et al., *J. Virol.*, 65, 4887 (1991). In this assay, MT-4 T-lymphoid cells were infected with HIV-1 (wild-type, unless otherwise indicated) by using a predetermined inoculum, and cultures were incubated for 24 h. At this time, ≦1% of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or $CIC_{95}$.

INHIBITION OF VIRUS SPREAD

A. Preparation of HIV-infected MT-4 cell Suspension

MT cells were infected at Day 0 at a concentration of 250,000 per ml with a 1:1000 dilution of HIV-1 strain IIIb stock (final 125 pg p24/ml; sufficient to yield <1% infected cells on day 1 and 25–100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% $CO_2$ atmosphere.

B. Treatment with Inhibitors

A matrix of nanomolar range concentrations of the pairwise combinations is prepared. At Day 1, aliquots of 125 µl of inhibitors are added to equal volumes of HIV-infected MT-4 cells (50,000 per well) in a 96-well microtiter cell culture plate. Incubation is continued for 3 days at 37° C. in 5% $CO_2$ atmosphere.

C. Measurement of Virus Spread

Using a multichannel pipettor, the settled cells are resuspended and 125 µl harvested into a separate microtiter plate. The supernatant is assayed for HIV p24 antigen.

The concentration of HIV p24 antigen is measured by an enzyme immunoassay, described as follows. Aliquots of p24 antigen to be measured are added to microwells coated with a monoclonal antibody specific for HIV core antigen. The microwells are washed at this point, and at other appropriate steps that follow. Biotinylated HIV-specific antibody is then added, followed by conjugated streptavidin-horseradish peroxidase. A color reaction occurs from the added hydrogen peroxide and tetramethylbenzidine substrate. Color intensity is proportional to the concentration of HIV p24 antigen.

Calculation of Degree of Synergy or Enhanced Inhibition

When there is synergy pairwise combinations of inhibitors are found to exhibit markedly enhanced inhibition of virus spread, in comparison to each inhibitor alone, or in comparison to merely additive inhibition of each inhibitor.

The data is processed as follows: fractional inhibitory concentration ratios (FIC) are calculated according to Elion, et al., *J. Biol. Chem.*, 208, 477 (1954). The minimum sum of FICS, which is the maximum synergy, is determined for various pairwise combinations. The smaller the number, the greater the synergy.

EXAMPLE 1

A. Culture Preparation

Culture MA7074 was grown in seed and biotransformation media, respectively. Seed medium (KE medium) consisted of: 0.1% dextrose; 1% dextrin; 0.3% beef extract; 0.5% ardamine pH; 0.5% NZ amine type E; 0.005% $MgSO_4 \cdot 7H_2O$, and 0.037% $K_2HPO_4$ with pH adjusted to 7.1 with 0.05% $CaCO_3$. Biotransformation medium (soy-glucose) contained: 2% glucose; 0.5% soya meal; 0.5% yeast extract; 0.5% NaCl; 0.98% MES with pH adjusted to 7.0.

B. Biotransformation Screening

MA7074 was grown in KE seed medium. After overnight incubation at 27° C. with gyratory shake (220 rpm) two milliliters of each culture was transferred into 250 ml baffled flasks containing 50 ml of soy-glucose bioconversion medium. At zero time, 2.5 mg of Compound J, dissolved in 0.5 ml DMSO, was added to each flask and incubation continued as for seed culture. At various time intervals, a sample of the biotransformation culture was examined by HPLC. At the time of maximal conversion of the substrate, as determined by HPLC, the cultures were harvested and subjected to isolation, purification and characterization.

C. Isolation and Characterization of the Biotransformation Products

The content of thirty flasks, initially containing 75 mg of the HIV-protease inhibitor, Compound J, were pooled and centrifuged. The supernatant was recovered and extracted with methylene chloride (1500 ml) twice. The methylene chloride extract was concentrated to dryness and the residue was dissolved in methanol and filtered. The filtered methanol solution was applied onto a semi-preparative column and 3 ml fractions were obtained under a gradient solvent system. This solvent system consisted of 10 mM phosphate (reservoir A) and acetonitrile (solvent B) and the gradient was formed by raising the concentration of the solvent B in solvent A from 30% to 70% in forty minutes. Fractions eluting with the peak retention times of 18.24 and 19.37 minutes were separately collected and prepared for chemical characterization and biological activity evaluation. The first fraction (3.7 mg) was identified as 2,3-cis-hydroxy analogue and the second fraction (4.30 mg) proved to be 3-keto analogue of the HIV-protease inhibitor Compound J.

EXAMPLE 2

Two samples isolated from an incubation of the HIV protein inhibitor Compound J with bacterial culture MA7074 were characterized by mass spectral analysis. As shown below, one sample is Compound J hydroxylated on the indanyl ring with cis stereospecificity to 2-OH (Compound B1). The second sample is oxidized to a ketone at the 3 position of the indanyl ting (Compound F).

Mass spectra and daughter ion spectra were obtained by LC/MS/MS on a mass spectrometer using the ionspray interface. Samples were analyzed by direct injection in a mobile phase that consisted of 50% $CH_3CN$/50% 10 mM $NH_4OAc$/0.1% TFA. Positive ion detection was used.

The mass spectrum of J gave an $(M+H)+=614$, which indicated a molecular weight of 613 Da. Four key fragment ions in the daughter ion spectrum of J at m/z 513, 465, 421, and 338, made it possible to determine the general site of metabolism for these samples. The following table summarizes the results of the analysis of these spectra and includes samples of MA7074 biotransformation products (68051-5×2 and 68051-5×3) as well as products from other microorganisms:

TABLE

| Sample (Compound) | Mol. Weight | Addition of: | Site of Addition |
|---|---|---|---|
| 68051-5 X1 | 645 | two hydroxyls | phenyl, indanyl |
| 68051-5 X2 (B1) | 629 | hydroxyl | indanyl |
| 68051-5 X3 (F) | 627 | ketone | indanyl |
| 68051-9 A* | 629 | oxygen | pyridine |
|  | +629 | hydroxyl | indanyl |
| 68051-9 B | 629 | hydroxyl | indanyl |
| 68051-9 C | 629 | hydroxyl | indanyl |
| 68051-12 F1 | 629 | hydroxyl | phenyl |
| 68051-12 F2 | 629 | hydroxyl | indanyl |
| 68051-12 F3 | 629 | oxygen | pyridine |

*Sample was determined to be a mixture of two oxygenated compounds

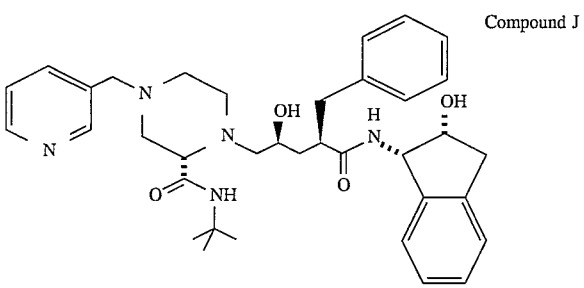

Compound J

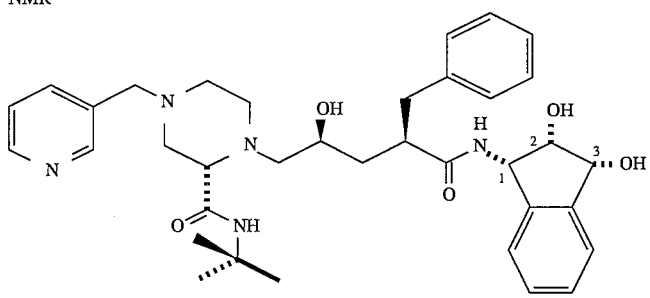

NMR

B1

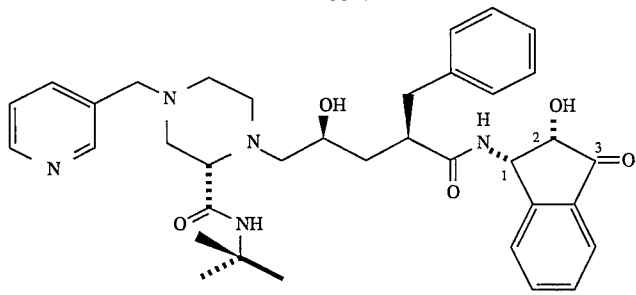

F

The key nmr feature for Compound B is the presence of a new signal at 4.95 ppm which was identified as H-3. The chemical shift is almost identical to H3 in the trans 3-OH analog, 58504-123.

The structure for Compound F was deduced from the appreciable downfield displacements of all of the indane aromatic protons and the appearance of H-2 as a simple doublet. The lack of additional splitting implies the absence of a proton attached to C3.

Stereochemical Assignments of Compound B1

The above biotransformation products derived from Compound J:

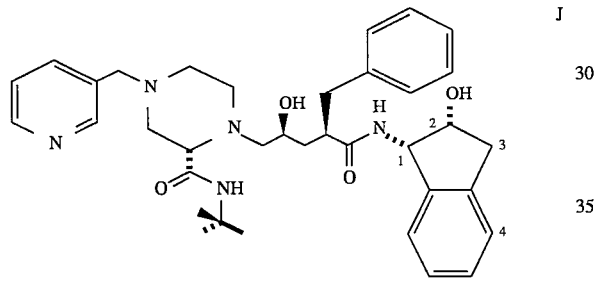

J identified as 3-hydroxy stereoisomers as illustrated:

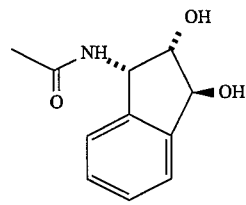

58504-123

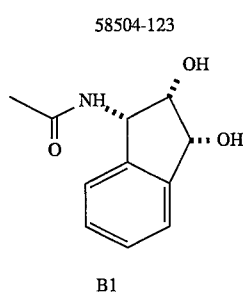

B1

The close correspondence of chemical shifts and especially JH3, H2 in 123 and B1 precluded their use for stereochemical assignments. One distinctive feature in B1, the 0.9 Hz secondary splitting of H3, is diagnostic of coupling with H4, and indicates that H3 is inclined about 30° from the plane of the aromatic ring.

In contrast, the absence of comparable splitting for H3 in 123 implies that the angle of inclination between H3 and the aromatic ring is this isomer is close to zero. These observations which suggested NOE experiments as a possible approach were supported by x-ray data on a related indane derivative. Based on the x-ray diagram one would predict the following results from NOE experiments:

A: Irradiation of H2
  1. Comparable NOE signals from H1 and H3 in B1, i.e., isomer in which H3 is cis/gauche with respect to H1 and H2.
  2. NOE signal from H3 weaker than H1 in 123, i.e., isomer in which H3 is trans with respect to H1 and H2.

B: Irradiation of H3
  1. NOE signals from H1 and H2 in B1.
  2. Weaker NOE signal from H2; very weak or non-detectable NOE from H1 in 123.

All of these predictions were verified.

EXAMPLE 3

HIV Protease Inhibitory Activity of Compound J Bioconversion Products

Seven Compound J bioconversion products were assayed for in vitro HIV protease inhibitory by the assay for inhibition of microbial expressed HIV Protease, protocol given above. Two of the bioconversion products were isolated from MA7074 incubations, Compounds B1 and F. The $IC_{50}$ of the parent Compound J was divided by the $IC_{50}$ of each test compound and multiplied by 100 in order to calculate the percent potency of each compound relative to J.

In some cases, the dilution of the test compound was based on nominal weight. In other cases, especially when the weight was less than 250 μg, the concentration was checked by HPLC using J as standard.

| Compound | Wt. Rec'd | % Potency Relative to Compound J | |
|---|---|---|---|
| | | Based On Nominal Wt. | Based on HPLC |
| A (2,3-Trans-OH) | 750 μg | 27% | —[a] |
| B1 (2,3-Cis-OH) | 240 μg | —[a] | 115% |
| C (5- or 6-OH-Indane) | 50 μg | 8.6% | 86% |
| D (p-OH-Phenyl) | 50 μg | 3.1% | 31% |
| E (N-Oxide) | 250 μg | 34% | —[a] |
| F (3-Ketone) | 1000 μg | 16% | —[a] |

[a]Not calculated

EXAMPLE 4

Preparation of Amide 1

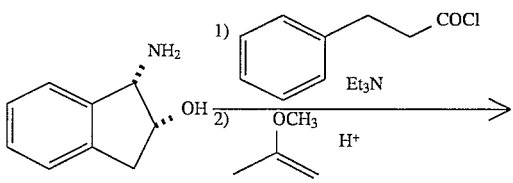

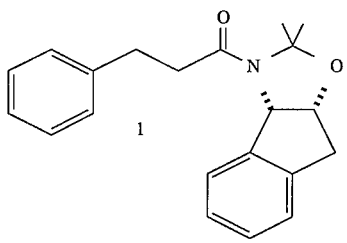

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature was kept between 14–24° C. with an ice-water cooling batch. After addition, the mixture was aged at 18°to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/ $K_2HPO_4$), 1.0 mL/min, injection volume=20 mL, detection= 200 nm, sample preparation=500 ×dilution. Approximate retention times:

| retention time (min) | identity |
|---|---|
| 6.3 | cis-aminoindanol |

The reaction was treated with pyridinium p-toluene-sulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 1 (86.4%, 98 area % by HPLC), $^1H$ NMR (300.13 MHz, $CDCl_3$, major rotamer) δ 7.36–7.14 (m, 9 H), 5.03 (d, J=4.4, 1 H), 4.66 (m, 1 H) 3.15 (m, 2 H), 3.06 (br s, 2 H), 2.97 (m, 2 H), 1.62 (s, 3 H), 1.37 (s, 3 H); $^{13}C$ NMR (75.5 MHz, $CDCl_3$, major rotamer) $δ_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1. Anal. Calcd for $C_{21}H_{23}NO_2$: C, 78.47; H, 7.21; N, 4.36. Found: C, 78.65; H, 7.24; N, 4.40.

EXAMPLE 5

Preparation of Epoxide 3

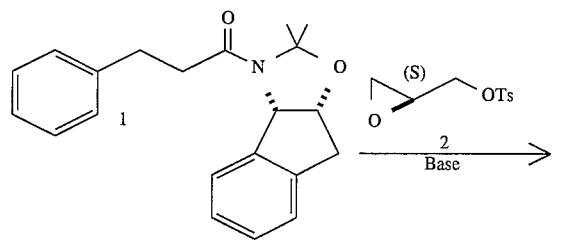

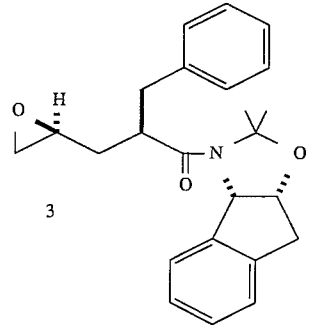

A solution of acetonide 1 (1000 g, 3.11 mol) and 2(S)-glycidyl tosylate 2 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide ($LiN[(CH_3)_3Si]_2$)(2.6 L, 1.38M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection= 254 nm, sample preparation=100×dilution. Approximate retention times:

| retention time (min) | identity |
|---|---|
| 5.5 | amide 1 |
| 6.5 | glycidyl tosylate 2 |
| 13.5 | epoxide 3 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous $NaHCO_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 3 (61.2%, 98.7 area % of the major epoxide by HPLC): $_{13}$C NMR (75.5 MHz, CDCl$_3$) δ 171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 6

Preparation of penultimate 6

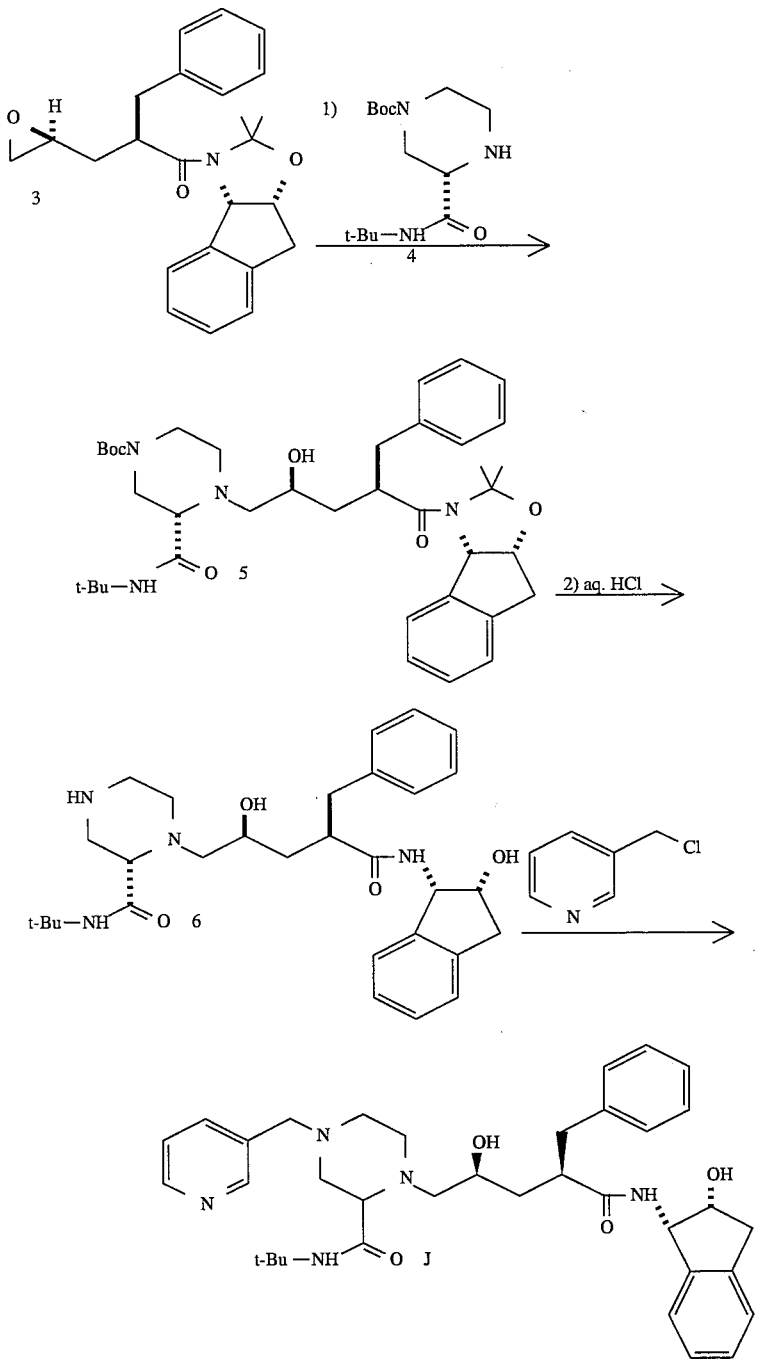

A slurry of the 2(S)-t-butylcarboxamide-4-N-Boc-piperazine 4 (1950 g, 6.83 mol, >99.5% ee) (ee=enantiomeric excess) and the epoxide 3 (2456 g, 97.5:2.5 mixture of 4S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C.). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM ($KH_2PO_4/K_2HPO_4$), 1.0 mL/min, detection=220 nm, sample preparation=2 μL, reaction mixture diluted to 1 mL in acetonitrile. Approximate retention times:

| retention time (min) | identity |
|---|---|
| 4.8 | piperazine 4 |
| 8.9 | epoxide 3 |
| 15.2 | coupled product 5 |

After 28 h, the remaining epoxide 3 and coupled product 5 (by HPLC analysis) were 1.5 area % and 91–93 area %, respectively. The mixture was cooled to 0° to 5° C. and 20.9 L of 6N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
|---|---|
| 7.0 | cis-aminoindanol |
| 11.9 | penultimate 6 |
| 15.1 | coupled product 5 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 6 in ethyl acetate was 86.5%. The penultimate compound 6 in DMF was directly used in the next step without further purification. For isolated 6: $^{13}$C NMR (75.4 MHz, CDCl3) δ 175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

To 10.0 g (0.019 mol) of N-(2(R)-hydroxy-1(S)-indanyl)-2(R)-phenylmethyl-4(S)-hydroxy)-5-(1 (-2(S)-N-(t-butyl-carbamoyl)-piperazinyl)-pentaneamide 6 and 3.45 g (0.021 mol) of 3-picolyl chloride dissolved in 40 mL of DMF was added 5.85 mL (0.042 mol) of triethylamine. After 3 hours an additional 0.313 g of 3-picolyl chloride was added. After an additional 2 hours the reaction was diluted with 400 mL of EtOAc and washed with water (3×75 mL), brine (1×100 mL), dried over $MgSO_4$ and concentrated. The residue was triturated with 30 mL of EtOAc and the resulting white precipitate was collected. Further recrystallization from EtOAc provided the Compound J product (mp 167.5°–168° C.).

EXAMPLE 7

Pyrazine-2-tert-butyl carboxamide 9

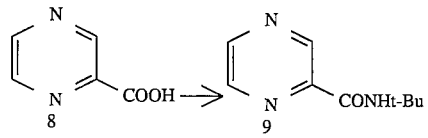

| 2-Pyrazinecarboxylic acid (8) | 3.35 kg (27 mol) |
|---|---|
| Oxalyl chloride | 3.46 kg (27.2 mol) |
| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 8 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition CO and $CO_2$ were evolved. The HCl that was formed remained largely in solution. A precipitate was present which is probably the HCL salt of the pyrazine acid chloride. Assay of the acid chloride formation was carded out by quenching an anhydrous sample of the reaction with t-butylamine. At completion <0.7% of acid 8 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 8=10.7 min, amide 9=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butyla-nunonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 9 was concentrated at 10 mbar to 25% of the original volume. 30 L of 1-propanol were added, and the distillation was continued until a final volume of 20 L was reached.

At this point, the EtOAc was below the limit of detection in the $_1$H NMR (<1%). The internal temperature in this solvent change was <30° C. A 1-propanol/EtOAC solution of 3 was stable to reflux atatmospheric pressure for several days. Evaporation of an aliquot gave a tan solid m.p.

87°–88° C. $^{13}$C NMR (75 MHz, CDCl$_3$, ppm) 161.8, 146.8, 145.0, 143.8, 142.1, 51.0, 28.5.

EXAMPLE 8

Rac-2-Tert-Butyl-Carboxamide-Piperazine 10

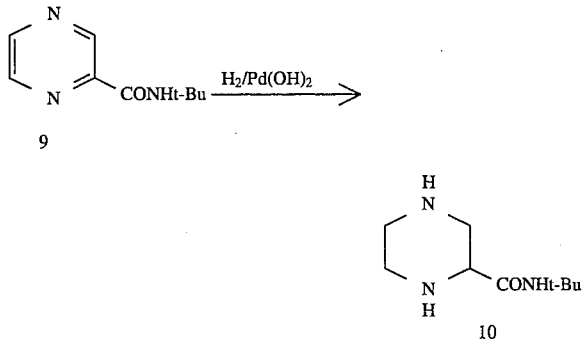

Materials

Pyrazine-2-tert-butylcarboxamide 9 2.4 kg (13.4 mol) in 1-Propanol solution 12 L 20% Pd(OH)$_2$/C 16 wt. % water 144 g.

The pyrazine-2-tert-butylcarboxamide 9/1-propanol solution was placed into the 5 gal autoclave. The catalyst was added and the mixture was hydrogenated at 65° C. at 40 psi (3 atm) of H$_2$.

After 24 h the reaction had taken up the theoretical amount of hydrogen and GC indicated <1% of 9. The mixture was cooled, purged with N$_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 9=7.0 min, 10=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 10 is 133 g/L.

Evaporation of an aliquot gave 10 as a white solid m.p. 150°–151° C.; $^{13}$C NMR (75 MHz, D$_{20}$, ppm) 173.5, 59.8, 52.0, 48.7, 45.0, 44.8, 28.7.

EXAMPLE 9

(S)-2-tert-Butyl-carboxamide-piperazine bis (S)-Camphorsulfonic acid salt (S)-11

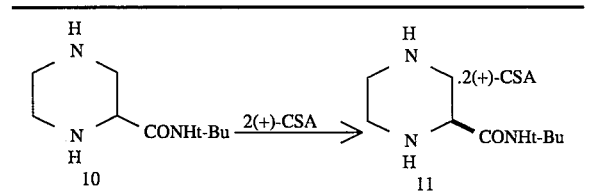

Materials

| rac-2-tert-Butyl-carboxamide-piperazine 10 in 1-Propanol Solution | 4.10 kg (22.12 mol) in 25.5 Kg solvent |

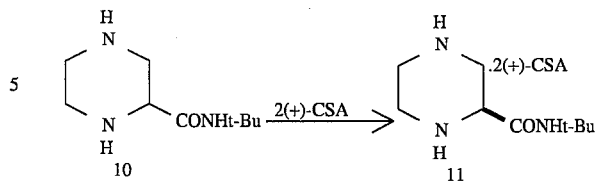

| | |
|---|---|
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 10 in 1-propanol was charged to a 100 L flask with an attached batch concentrator. The solution was concentrated at 10 mbar and a temperature <25° C. to a volume of ca 12 L.

At this point the product had precipitated from the solution, s but went back into a solution when the mixture was heated to 50° C.

Analysis of a homogeneous aliquot indicated that the concentration of 10 was 341 g/L. The concentration was determined by HPLC: 25 cm Dupont Zorbax RXC8 column with 1.5 mL/min flow and detection at 210 nm, isocratic (98/2) CH$_3$CN/0.1% aqueous H$_3$PO$_4$. Retention time of 10: 2.5 min.

Acetonitrile (39 L) and water (2.4 L) were added to give a clear, slightly brown solution.

Determination of the water content by KF titration and CH$_3$CN/1-propanol ratio by $_1$H NMR integration showed that the CH$_3$CN/1-propanol/H$_2$O ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the CH$_3$CN/1-propanol/H$_2$O 26/8/1.6 solvent mixture. It was dried at 35° C. in the vacuum oven with N$_2$ bleed to give 5.6 Kg (39%) of 11 as a white crystalline solid m.p. 288°–290° C. (with decomp.) [α]D$^{25}$= 18.9° (c=0.37, H$_2$O). $^{13}$C NMR (75 MHz, D$_2$O, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 11 (33 mg) was suspended in 4 mL of EtOH and 1 mL of Et$_3$N. Boc$_2$O (11 mg) was added and the reaction mixture was allowed to age for 1 h. The solvent was completely removed in vacuo, and the residue was dissolved in ca. 1 mL of EtOAc and filtered through a Pasteur pipet with SiO$_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 10

(S)-2-tert-Butylcarboxamide-4-tert-butoxycarbonyl-piperazine 4 from salt 11

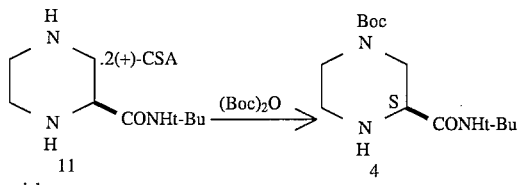

Materials

| | |
|---|---|
| (S)-2-tert-Butyl-carboxamide-piperazine Bis (S)-(+)-CSA salt 11, 95% ee | 5.54 Kg (8.53 mol) |
| Di-tert-butyl dicarbonate | 1.86 Kg (8.53 mol) |
| Et₃N | 5.95 L (42.6 mol) |
| EtOH Punctilious 200 proof | 55 L |
| EtOAc | 2 L |

To the (S)-CSA salt 11 in a 100 L 3-neck flask with an addition funnel under $N_2$ was added EtOH, followed by triethylamine at 25° C. The solid dissolved readily on the addition of the Et3N. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC: 25 cm Dupont Zorbax RXC8 column with 1 mL/min flow and detection at 228 nm, isocratic (50/50) $CH_3CN/0.1M$ $KH_2PO_4$ adjusted to pH=6.8 with NaOH. Retention time of 4=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area % by HPLC, R-isomer below level of detection) of 4 as a slightly tan powder. $[\alpha]D^{25}$=22.0° (c=0.20, MeOH), m.p. 107° C.; $^{13}C$ NMR (75 MHz, CDCl₃, ppm) 170.1, 154.5, 79.8, 58.7, 50.6, 46.6, 43.6, 43.4, 28.6, 28.3.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. A pure culture of *Streptomyces sp.* MA 7074 having ATCC number 55605.

* * * * *